(12) United States Patent
Emmerson et al.

(10) Patent No.: US 7,715,005 B2
(45) Date of Patent: May 11, 2010

(54) MULTIWAVELENGTH OPTICAL SENSORS

(75) Inventors: Gregory Daniel Emmerson, Highfield (GB); Corin Barry Edmund Gawith, Highfield (GB); Peter George Robin Smith, Highfield (GB)

(73) Assignee: University of Southampton, Hampshire (GB)

( * ) Notice: Subject to any disclaimer, the term of this patent is extended or adjusted under 35 U.S.C. 154(b) by 568 days.

(21) Appl. No.: 11/572,129

(22) PCT Filed: Jul. 7, 2005

(86) PCT No.: PCT/GB2005/002680

§ 371 (c)(1),
(2), (4) Date: Jan. 15, 2007

(87) PCT Pub. No.: WO2006/008447

PCT Pub. Date: Jan. 26, 2006

(65) Prior Publication Data

US 2008/0204747 A1    Aug. 28, 2008

(30) Foreign Application Priority Data

Jul. 15, 2004    (GB)    ................... 0415881.2

(51) Int. Cl.
*G01J 3/30*    (2006.01)
(52) U.S. Cl. ......................... 356/328; 385/12
(58) Field of Classification Search ................. 356/328; 385/12
See application file for complete search history.

(56) References Cited

U.S. PATENT DOCUMENTS 3,539,262 A    11/1970    Pryor
(Continued)

FOREIGN PATENT DOCUMENTS

EP    1154269    11/2001
(Continued)

OTHER PUBLICATIONS

J Bowen, LJ Noe, BP Sullivan, K Morris, V Martin and G Donnelly, "Gas phase detection of trinitrotoluene utilizing a solid-phase antibody immobilized on a gold film by means of surface plasmon resonance spectroscopy", Appl. Spectrosc., 57(8), 906-914, 2003.
(Continued)

*Primary Examiner*—Kara E Geisel
(74) *Attorney, Agent, or Firm*—Renner, Otto, Boisselle & Sklar, LLP

(57) ABSTRACT

An optical sensor comprises at least two planar Bragg gratings defined on a single substrate and arranged to receive light from a light source, each grating having a wavelength filtering response that varies with an effective modal index experienced by light propagating in the Bragg grating and a Bragg wavelength different to those of the other gratings, and at least one sample window overlying one or more of the gratings that can receive a sample of fluid that affects the effective modal index and response of the grating, the gratings filtering the light and outputting the filtered light for spectral analysis, from which the refractive index and related properties of the fluid can be determined. One or more of the gratings can be a reference grating used to compensate for temperature and other disturbances to the sensors. Gratings may have individual sample windows for testing separate fluid samples, or may share a common window so that a single fluid can be tested using several gratings.

27 Claims, 4 Drawing Sheets

U.S. PATENT DOCUMENTS

| | | | |
|---|---|---|---|
| 6,072,567 A * | 6/2000 | Sapack | 356/32 |
| 6,277,330 B1 | 8/2001 | Liu et al. | |
| 7,157,693 B2 * | 1/2007 | Thingbo et al. | 385/12 |
| 2003/0098971 A1 * | 5/2003 | Laffont et al. | 356/128 |
| 2005/0068525 A1 * | 3/2005 | Taverner et al. | 356/327 |
| 2005/0075704 A1 * | 4/2005 | Tu et al. | 607/88 |
| 2005/0135723 A1 * | 6/2005 | Carr et al. | 385/12 |

FOREIGN PATENT DOCUMENTS

| | | |
|---|---|---|
| EP | 1548424 | 6/2005 |
| GB | 2395797 | 6/2004 |
| WO | 0029883 | 5/2000 |

OTHER PUBLICATIONS

RG Heideman, RPH Kooyman and J Greve, "Performance of a highly sensitive optical wave-guide Mach-Zehnder interferometer immunosensor", Sensors and Actuators B-Chemical, 10(3), 209-217, 1993.

K Tiefenthaler and W Kukosz, "Integrated optical switches and gas sensors", Optics Letters, 10(4), 137-139, 1984.

W Lukosz, D Clerc and PhM Nellen, "Input and output grating couplers as integrated optical chemo- and biosensors", Sensors and Acuators A, 25-27, 181-184, 1991.

A Asseh, S Sandgren, H Ahlfeldt, B Sahlgren, R Stubbe and G Edwall, "Fiber optical Bragg grating refractometer", Fiber and Integrated Optics, 17(1), 51-62, 1998.

A Iadicicco, A Cusano, A Cutolo, R Bernini and M Giordano, "Thinned fiber Bragg gratings as high sensitivity refractive index sensor", IEEE Photonics Technology Letters, 16(4), 1149-1151, 2004.

X Chen, K Zhou, L Zhang and I Bennion, "Optical chemsensors utilizing long-period fiber gratings UV-inscribed in D-fiber with enhanced sensitivity through cladding etching", IEEE Photonics Technology Letters, 16(5), 1352-1354, 2004.

BJ Luff, JS Wilkinson, G Perrone, "Indium tin oxide overlayered waveguides for sensor applications", Applied Optics, 36(27), 7066-7072, 1997.

W Lukosz, "Integrated optical chemical and biochemical sensors", Sensors and Actuators B, 29, 37-50, 1995.

R Kashyap, "Photosensitive optical fibers: Devices and applications", Optical Fiber Technology, 1, 17-34, 1994.

Veldhuis G J et al: "An integrated optical Bragg-reflector used as a chemo-optical sensor" Pure and Applied Optics, Bristol, GB, vol. 7, No. 1 Jan. 1998, pp. L23-L26, XP002087839.

Schroeder K et al: "A Fibre Bragg Grating Refractometer", Measurement Science and Technology, IOP Publishing, Bristol, GB, vol. 12. No. 7, Jul. 2001, pp. 757-764, XP001209001.

Ctyroky J et al: "Modeling of the surface plasmon resonance waveguide sensor with Bragg Grating" Optical and Quantum Electronics Kluwer Academic Publishers Netherlands, vol. 31, No. 9-10, Oct. 1999, pp. 927-941, XP002346149.

* cited by examiner

MULTIWAVELENGTH OPTICAL SENSORS

This application is a national phase of International Application No. PCT/GB2005/002680 filed Jul. 7, 2005 and published in the English language.

BACKGROUND OF THE INVENTION

The present invention relates to optical sensors based on planar waveguide gratings for sensing the refractive index of fluid samples and parameters and characteristics related thereto.

Measurement of the optical refractive index of fluids is of importance in fields including bioanalysis and biosensing. Different fluids, or concentrations of the same fluid, have different refractive indices so that the fluids can be identified or distinguished from refractive index measurements. The refractive index or change in refractive index of a fluid can be used to determine many biologically important measurands such as protein concentrations and glucose levels. In other fields, refractive index measurements are used in applications as diverse as process control and the detection of explosives [1].

Various devices and techniques for measuring refractive index are known. These include the Abbe-type refractometer, and sensors based on surface plasmon resonance. Optical waveguides may also be used. The presence of a liquid adjacent to an optical waveguide can alter the effective modal index of light propagating within the waveguide. This modification of index can be measured using techniques that are sensitive to changes in optical path length. For example, interferometer structures have been used to measure index changes and hence to sense the presence of proteins [2].

An alternative to interferometric measurement is to use optical waveguide gratings, where the reflective properties of a grating, which depend on refractive index, are modified by the index of a liquid in contact with the waveguide. An early device of this type used planar optical waveguides with surface relief gratings, in which adsorption and desorption of gas on the waveguide surface changed the refractive index and allowed the gas to be sensed [3]; other planar grating configurations have been proposed for integrated optical biological and chemical sensors [4]. Other grating-based devices have used fibre Bragg gratings [5]. Proposals have included thinning of the fibre with wet-etching to increase sensitivity [6], and the use of long period gratings in D-fibre, found to be more sensitive than gratings in standard telecom fibre [7]. However, the use of fibre gratings requires tedious working of the fibre to expose the waveguiding core to the liquid, such as by etching, which is difficult to control in a fibre geometry, or mounting the fibre in a block and polishing it down to access the core. Planar waveguide implementations are preferable in that it is typically easier to gain access to the propagating optical mode.

SUMMARY OF THE INVENTION

A first aspect of the present invention is directed to an optical sensor comprising: a substrate; at least two planar Bragg gratings defined within one or more optical waveguides in the substrate, each Bragg grating having a wavelength filtering response that varies with an effective modal index experienced by light propagating in the Bragg grating and that has a characteristic Bragg wavelength different from the Bragg wavelengths of the other Bragg gratings; and at least one sample window overlying and associated with at least one of the Bragg gratings and arranged to receive a sample of fluid such that the presence of a sample of fluid affects the effective modal index experienced by light propagating in the associated Bragg grating and hence modifies the wavelength filtering response of that Bragg grating; the Bragg gratings being arranged to receive light from a light source, filter the light, and output the filtered light for detection by a spectrally resolving optical detector.

A sensor incorporating a number of gratings on a single substrate is advantageous in that many configurations of sensor can be implemented, offering simultaneous testing of multiple samples or testing under different parameters, with the different Bragg wavelengths giving a spectral element to measurements made with the sensor, which can yield detailed information about fluids and allow different fluids to be discriminated. Also, the use of different wavelengths allows unique accessing of the different gratings just by using light of a suitable wavelength, so that coupling of light into and out of the gratings and subsequent analysis of the detected light can be very straightforward. The light output by the sensor can be used to measure refractive index and dispersion, to determine parameters related to refractive index, to investigate layers within a fluid sample or the spatial distribution of the fluid along the length of the sample window, and/or to identify fluid types, among other applications. Positioning the gratings on one substrate means that they have more similar environments so that the output of the sensor is less subject to errors caused by disturbances, since all gratings are equally disturbed so that their relative outputs are not affected. The fabrication and structure of the sensor can be simple; direct ultraviolet writing techniques can be used to define the components of the whole sensor in a single processing step. Planar waveguide gratings are a particularly convenient way of providing reflecting elements with the required wavelength filtering responses, since they are compact and robust, and can be fabricated accurately with a wide range of responses, particularly by means of ultraviolet writing.

In some embodiments, the at least one sample window is associated with each of the at least two Bragg gratings, so that all of the least two Bragg gratings may be provided with a sample of fluid. This allows every grating to be used for fluid testing and measurement, if desired. The at least one sample window may comprise a single sample window shared by all of the at least two Bragg gratings so that a sample of fluid received by the sample window affects the effective modal index of light propagating in all of the at least two Bragg gratings. Thus, every grating is used to interrogate a single fluid sample, so that detailed spectral information about fluid properties can be determined as simply as possible. Alternatively, the at least one sample window may comprise a separate sample window associated with each of the at least two Bragg gratings, so that each of the at least two Bragg gratings may be provided with a separate sample of fluid. This allows a number of different samples to be looked at simultaneously, and may also be relevant in cases where window dimensions are significant, for example if the available fluid samples are very small.

The at least two Bragg gratings may comprise one or more pairs of Bragg gratings, each pair of Bragg gratings comprising a sensing grating having an associated sample window and a reference grating, the sensing grating and the reference grating having Bragg wavelengths sufficiently closely separated that the gratings have substantially the same modal confinement. For example, the sensing grating and the reference grating may have Bragg wavelengths separated by an amount in the range of 2 to 10 nm. The use of reference gratings allows compensation to be made for thermal variation and other disturbances that may induce errors. Comparison of the responses of the reference and sensing gratings allows index changes induced by a fluid sample applied to the sensing grating to be isolated from changes arising from unrelated perturbations. This is made particularly accurate since the gratings are on the same substrate, so that the environments of the reference and sensing gratings are as similar as possible except for the fluid sample. To further liken the environments of the reference and sensing gratings, the reference grating may have an associated sample window, separate from the sample window associated with the sensing grating. A reference fluid can be applied to the reference grating, to give the two gratings a similar response to temperature changes, for example. Also, the reference grating and the sensing grating may be defined within a single waveguide.

In some embodiments, the at least two Bragg gratings may comprise a plurality of Bragg gratings divided into groups of Bragg gratings, the Bragg gratings within each group having Bragg wavelengths separated by a first separation, and each group having an average Bragg wavelength separated from average Bragg wavelengths of other groups by a second separation greater than the first separation. The second separation may be at least ten times greater than the first separation, for example. The first separation may be in the range of 2 to 10 nm.

Advantageously, the one or more optical waveguides may be configured for single mode propagation of light.

At least one of the at least one sample windows may comprise a portion of a cladding layer overlying a core of the optical waveguide in which the associated Bragg grating is defined, such that a sample of fluid received by the sample window is in contact with the cladding layer. Further, the sensor may comprise two or more sample windows in each of which the portion of the cladding layer has a different thickness. Additionally or alternatively, at least one of the at least one sample windows may comprise an exposed portion of a core of the optical waveguide in which the associated Bragg grating is defined, such that a sample of fluid received by the sample window is in contact with the core. These options can be used to select the sensitivity of the grating to the fluid, with further flexibility available in the former option by choosing the thickness of the cladding layer to determine the proximity of the fluid to the core. In the latter option, the exposed portion of the core may have a thickness less than a thickness of the core in adjacent portions of the optical waveguide in which the associated Bragg grating is defined. This arrangement can be used to give single mode waveguiding through the grating to overcome modal disturbance that can arise from the change of waveguide structure at the edges of the sample window.

The or each Bragg grating having an associated sample window may be defined in an optical waveguide having a core that has a tapering variation in refractive index along its length, to reduce abrupt changes in the effective model index at edges of the sample window. A waveguide structured in this way also helps to overcome modal disturbances at the window boundaries, by reducing reflections that may occur at an abrupt structural boundary. Similarly, the at least one sample window may have one or more edges that are angled with respect to a light propagation direction in the optical waveguide in which the associated Bragg grating is defined, to reduce reflections of light propagating in the Bragg grating.

The one or more optical waveguides may comprise one or more layers that modify waveguiding properties of the one or more optical waveguides. Additional layers can be used to pull the optical field of light propagating in the waveguide towards or away from the sample window, allowing tailoring of the sensitivity of the sensor to fluid received in the window.

Sensors according to the present invention may be used to make direct refractive index measurements, or to measure or detect fluid characteristics that vary with refractive index. This approach can be extended by simple modifications to the sensor. For example, at least one of the at least one sample windows may be provided with a surface coating of a chemically selective material operable to bind with molecules that may be present in a sample of fluid to be received by the sample window, the binding causing an alteration of the effective modal index of light propagating in the associated Bragg grating. Thus, chemically and biochemically reactive substances can be detected, for example, testing for the presence of particular antibodies in biological samples. Also, at least one of the at least one sample windows may be provided with a surface layer of a metal having a surface plasmon that may be altered by a sample of fluid to be received by the sample window, the alteration in the surface plasmon causing an alteration of the effective modal index of light propagating in the associated Bragg grating.

The sensor may further comprise a heating or cooling device operable to modify the temperature of the substrate such that each of the at least two Bragg gratings have substantially the same temperature. Measurements can be made at different fluid temperatures by heating the gratings and the fluid sample(s). The fact that all the gratings, including any reference gratings, are all on the same substrate means that they are similarly heated, which eliminates errors that could arise from the temperature-dependence of the wavelength filtering responses in the event of unequal heating.

The optical sensor may comprise gratings according to the preceding examples and embodiments to which a user can connect light sources and optical power detectors as required. However, other embodiments may additionally include these components, perhaps mounted on a single substrate with the sensing and analysing elements. In some embodiments, the optical sensor may further comprise one or more light sources operable to deliver light to the at least two Bragg gratings such that each Bragg grating receives light having a spectral bandwidth covering at least part of its wavelength filtering response. Also, the sensor may further comprise a spectrally resolving optical detector operable to detect and spectrally resolve light output by each of the Bragg gratings.

A second aspect of the present invention is directed to a process control system operable to control apparatus for performing a process, comprising: at least one optical sensor according to the first aspect and arranged to receive samples of fluid utilised in or generated by the process; an optical source operable to generate light covering the wavelength filtering response or responses of the Bragg gratings of at least one optical sensor; a spectrally resolving optical detector operable to receive and perform spectral analysis of light from the at least one optical sensor and to generate one or more control signals for controlling the apparatus in response to the analysis; and an optical routing device connected to the at least one optical sensor, the optical source and the optical detector, and operable to receive light from the optical source, distribute the light to the at least one optical sensor, receive light output by the at least one optical sensor, and deliver the output light to the optical detector.

A third aspect of the present invention is directed to an optical sensor network comprising: a plurality of optical sensors according to the first aspect; an optical routing device connected to each of the plurality of optical sensors and operable to receive light from a light source, distribute the light to the plurality of optical sensors, receive light output by the plurality of optical sensors, and output the received light for spectral analysis. The network may further comprise an optical source operable to generate light covering the wavelength filtering responses of the Bragg gratings of the plurality of optical sensors and arranged to deliver the light to the optical routing device; and a spectrally resolving optical detector arranged to receive light output from the optical routing device, and operable to perform spectral analysis of the light. Additionally, the optical sensor network may comprise a processor arranged to receive results of spectral analysis from the optical detector and operable to determine one or more properties of a sample or samples of fluid applied to the plurality of optical sensors from the results.

BRIEF DESCRIPTION OF THE DRAWINGS

For a better understanding of the invention and to show how the same may be carried into effect reference is now made by way of example to the accompanying drawings in which.

DETAILED DESCRIPTION

Figure 1:
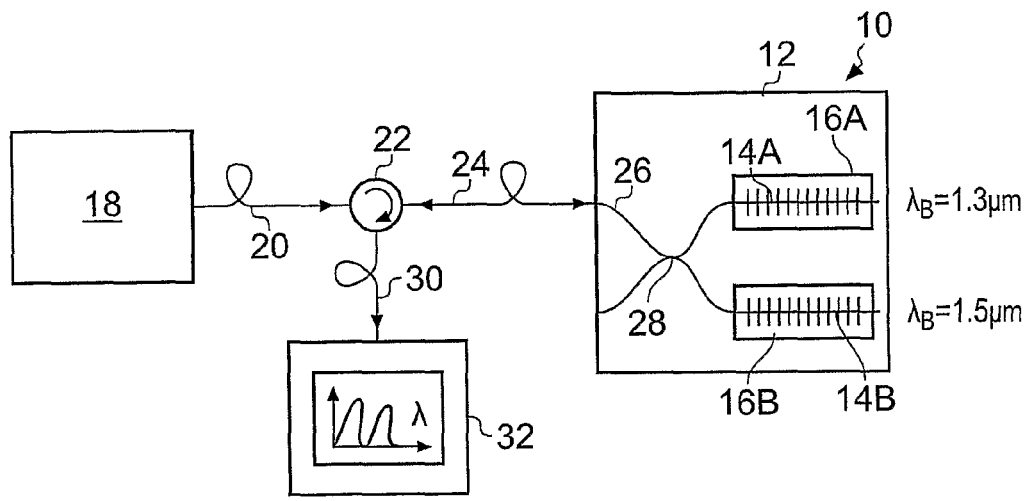
FIG. 1 shows a schematic representation of an optical sensor according to an embodiment of the present invention, comprising two Bragg gratings.

An optical reflective grating such as a Bragg grating comprises a periodic modification of refractive index within an optical waveguiding structure, where the waveguiding structure comprises a core surrounded by cladding material of a lower refractive index than the core. This structure guides optical waves by total internal reflection at the boundary between the two refractive indices. The grating reflects light propagating along the waveguide of wavelengths that falls within a bandwidth defined by the magnitude and dimensions of the periodic refractive index modification, and transmits light of other wavelengths.

If a region of the core of the waveguide is exposed or nearly exposed by removing all or part of a portion of the cladding, and a fluid applied to the region so that the optical field of light propagating in the waveguide extends into the fluid, the refractive index of the fluid modifies the effective modal index experienced by the propagating light. This is turn modifies the reflectivity properties of the grating, which can be measured. From this measurement, the refractive index of the fluid can be determined, which allows either direct refractive index measurements to be made, or other properties of the fluid to be determined if the relationship between these properties and refractive index is known.

A Bragg grating has a reflectivity peak at a Bragg wavelength $\lambda_{Bragg}$. This is defined by the Bragg relation $$n_{eff} = \lambda_{Bragg}/2\Lambda$$

where $n_{eff}$ is the effective modal index and $\Lambda$ is the grating period. Thus, if the grating period is known and the peak reflected wavelength is measured, the effective modal index can be calculated using the Bragg relation. From this, the refractive index of the fluid can be ascertained by calculation or by reference to the measured properties of calibrated standard liquids.

To achieve this, it is necessary to make accurate measurements of the wavelength of light reflected from or transmitted by the grating, to see how much the Bragg wavelength has been shifted by the presence of the fluid. Thus, a photodetecting device with adequate spectral resolution is used, such as an optical spectrum analyser (OSA), a spectrometer, or by using light from a tunable light source that is scanned in wavelength across the reflectivity bandwidth of the grating and recording the intensity reflected at each wavelength. The resulting measurement allows the properties of the fluid to be ascertained at the wavelength of measurement.

The present invention extends this concept by providing a sensor to determine fluid properties that incorporates several gratings on a single substrate, each grating having a reflectivity response with a different Bragg wavelength. Applying fluids to the various gratings allows refractive index and other fluid properties to determined at different wavelengths with a single device, so that dispersive properties (variation with wavelength) can be measured. Also, the various gratings can be uniquely accessed owing to their different wavelengths, so that results from different gratings can be readily distinguished, allowing a plurality of fluid samples to be measured at the same time. Also, the locating of several gratings on the same substrate improves results because the gratings each experience the same or similar environmental disturbances such as stresses or temperature changes that can modify the grating periods and the Bragg wavelengths and hence give erroneous results. In the present invention, each grating undergoes the same modification so that the relative shifts are the same.

FIG. 1 shows a schematic plan view representation of an example of a first, simple, embodiment of an optical sensor according to the present invention. The optical sensor 10 is formed on a single substrate 12, into which two planar waveguide gratings and associated waveguides are written. The first grating 14A, written into an optical waveguide, has a sample window 16A over it, which is a region of the substrate in which some or all of the cladding that defines the waveguiding properties is removed. A sample of fluid can be thereby be applied to the grating 14A by placing it in the sample window 16A. The grating 14A has a Bragg wavelength of 1.3 µm. The second grating 14B, written into a parallel waveguide, similarly has a sample window 16B over it, and has a Bragg wavelength of 1.5 µm.

Figure 2:
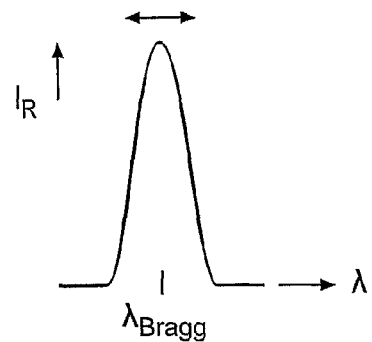
FIG. 2 shows an example wavelength filtering response of gratings included in the optical sensor of FIG. 1, demonstrating the operation of the sensor.

The Bragg wavelength of each grating is a peak in a reflectivity/transmissivity function that allows the gratings to operate as narrow-band optical filters, reflecting only light with wavelengths that satisfy the Bragg relation. These functions can be thought of as wavelength filtering responses. FIG. 2 shows the response of a grating 14 as a plot of wavelength $\lambda$ against reflected intensity $I_R$; this is the light that will be reflected from the grating if it is illuminated by light with a bandwidth broad enough to cover the bandwidth of the response peak. Thus, the sensor needs to be supplied with light of an appropriate spectral bandwidth. A light emitting diode may be suitable. A general broadband source may also be used. Depending on the range of wavelengths of gratings present on a single substrate, several sources can be combined to cover all the gratings. Operation of the sensor depends on shifting of the Bragg wavelengths of the gratings 14, so the input light also should have a bandwidth that encompasses the magnitude of the expected shift; this will depend on the range of fluids to be sensed by the sensor.

As explained, each grating 14 has some or all of its overlying cladding removed to allow the effective modal index to be affected, or altered, by the presence of a sample of fluid received by the sample window 16. Depending on the direction of change of the effective modal index, the Bragg wavelength of the grating is shifted, as indicated by the arrow in FIG. 2. The magnitude of the shift depends on the magnitude of the index change, which depends on the refractive index of the fluid sample. A fluid with a large index will increase the modal index and also the Bragg wavelength so that the response peak moves to the right in FIG. 2; a fluid with a small index has the opposite effect and moves the peak to the left.

To operate the sensor 10, light is directed along the waveguides to the gratings 14 from an optical source 18, operable to generate light at 1.3 µm and 1.5 µm. Two broadband sources may be combined to achieve this, to accommodate both the bandwidth of the gratings 14 and also the maximum anticipated shifts in Bragg wavelengths. The output from the optical source 18 passes along a first optical fibre 20, and into an optical circulator 22 which passes the light into a second optical fibre 24 that is coupled to an input waveguide 26 written into the substrate 12. The input waveguide is coupled to an integrated wavelength splitter 28 similarly written into the substrate, which splits the light into its two wavelength components and passes each component to the waveguide in which the relevant grating 14 is written. However, any light coupling and splitting device can be used to divide the light between the two waveguides. The different Bragg wavelengths make the gratings 14 self-selective with regard to wavelength, so that they will reflect at their own wavelengths and reject (transmit) light at other wavelengths. Hence light at wavelengths other than the relevant Bragg wavelength can be fed to a particular grating without detriment so that it is not necessary to spectrally separate the light before distributing it between the gratings.

Light reflected by the gratings 14 passes back along the waveguides to the splitter 28, where it is combined and coupled back to the input waveguide 26, the second optical fibre 24, and the circulator 22, which passes the reflected light to a third optical fibre 30. This feeds the light to an optical spectrum analyser (OSA) 32 for detection and spectral resolution/analysis. The OSA spectrally resolves the light it receives to give a reading of light intensity versus wavelength.

In this case, the reading shows two peaks, one from each grating 14. The shift in Bragg wavelength caused by the presence of fluid samples in the sample windows 16 can be measured from the reading, from which the refractive index and related properties of the fluid samples can be determined.

The presence of two gratings with different Bragg wavelengths combined with separate sample windows for each grating offers several uses of the sensor. Different fluids can be applied to each grating at the same time, and a single measurement made with light covering both filtering responses. The different reflected wavelengths present in the measured result can be used to distinguish between the gratings and hence the fluid samples, so that measurement and detection of two different samples can be performed simultaneously. Naturally, the gratings can also be used independently if desired. Also, if samples of the same fluid are applied to both gratings, measurements at two different wavelengths can be obtained. This is useful in that refractive index typically varies with wavelength (dispersion, $dn/d\lambda$), so that measurements at more than one wavelength can be used to determine this variation, or to take account of it if it is previously known and fluid properties related to refractive index are of interest. Also, different fluids can be distinguished or identified on the basis of measurements of the index variation, since fluids may have the same index at a single wavelength but have different dispersions. Index data obtained from the sensor can be fitted to power series-type representations of refractive index (Sellmeier equations).

This concept can be expanded to cover many gratings, so that detailed spectral information can be obtained, or to allow testing of many fluid samples by using wavelength to discriminate between them. To achieve this, it is necessary to provide light from a light source or combination of light sources to cover the bandwidths and shifts of all the gratings, to couple the light to each grating and collect it after filtering for spectral analysis. Any suitable combination of optical fibres, waveguides written into the substrate, couplers, splitters and circulators can be used to achieve this. Further, individual optical sources can be used, with their respective outputs coupled directly to individual gratings. Additionally, further components may be added to select a single polarisation of light entering the sensor; this reduces effects on the measured grating responses of birefringence in the sensor waveguides and gratings.

If a sensor is intended for testing many different samples, each grating should be provided with a separate sample window, as in the example of FIG. 1. However, if it is intended that a single fluid is to be tested at multiple wavelengths, the sensor can be simplified by providing a single sample window that extends across some or all the gratings, so that one sample can be applied to every grating under the window.

Figure 3:
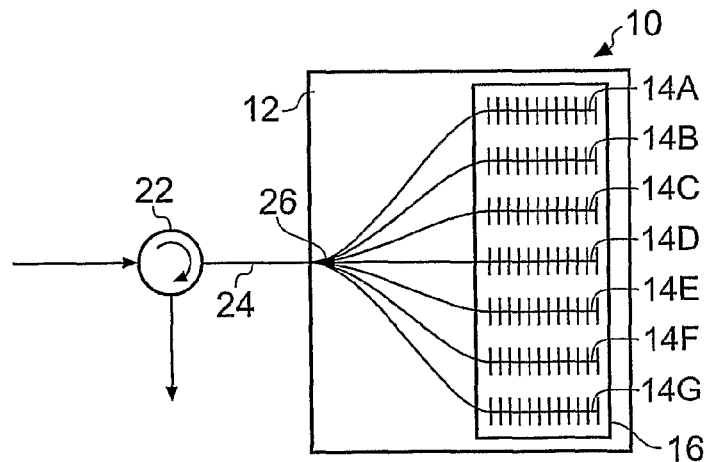
FIG. 3 shows a schematic representation of an optical sensor according to an further embodiment, comprising a plurality of Bragg gratings.

FIG. 3 shows schematic representation of an example of such a sensor. The sensor 10 in this case comprises seven gratings 14A-14G, each having a different Bragg wavelength, fabricated in parallel waveguides written on a single substrate 12. One sample window 16 covers all of gratings. The parallel waveguides are coupled to a single input/output waveguide 26 which is connected via an optical fibre 24 to a circulator 22 that delivers incoming light from a light source to the gratings, and then directs reflected light from the gratings to a spectrally resolving optical detector for spectral analysis. In the Figure, the connection between the waveguides is shown as a direct converging/diverging 1:n star coupler (where n is 7 in this example), but any equivalent coupling arrangement can be used, such as a cascade of y-splitters (1:2 couplers).

Further, the gratings need not be positioned within separate waveguides. Instead, two or more gratings can be arranged sequentially along a single waveguide. The self-selecting reflectivity of the individual gratings means that the single waveguide can carry light with a bandwidth covering the responses of all the gratings. The first grating reflects light with wavelengths within its response, and transmits all other wavelengths onto the following gratings, where the second grating reflects its wavelengths, and so on.

Figure 4:
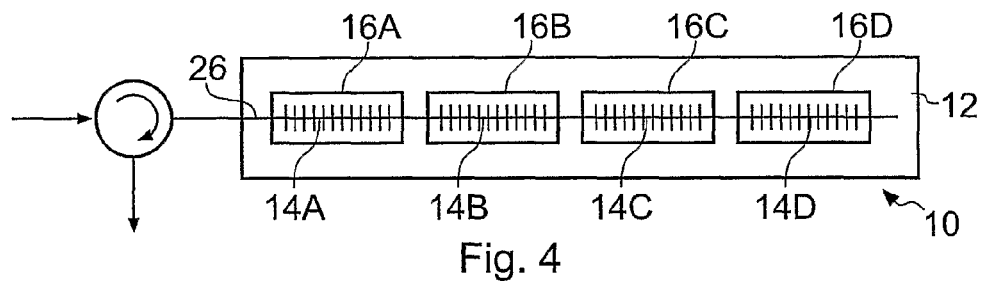
FIG. 4 shows schematic representation of an optical sensor according to a yet further embodiment, comprising a plurality of Bragg gratings within a single waveguide.

FIG. 4 shows a schematic representation of a sensor of this design. The sensor 10 features four gratings 14A-14D, each having a different Bragg wavelength, fabricated one after the other along the length of a single waveguide 26 written in a substrate 12. Incoming light is coupled directly into the waveguide 26 for transmission to the gratings, and the reflected light is collected for spectral measurement as it is emitted from the waveguide 26.

Further embodiments of the invention include one or more gratings used as reference gratings. As before, each of these gratings has a different Bragg wavelength from the other gratings in the sensor. The purpose of a reference grating is to allow compensation for environmental disturbances and other perturbations that may disrupt the performance of gratings being used to measure fluids (which may be thought of as sensing gratings). These include changes in temperature, or stresses being applied to the substrate. Such disturbances are liable to temporarily modify the structures of the gratings and produce a shift in Bragg wavelength that is unrelated to that caused by an applied fluid sample but which cannot be distinguished therefrom in the measured spectrum. To address this, a reference grating can be provided to which no fluid sample is applied. Any shift in the spectrum of light reflected from the reference grating cannot be caused by the fluid sample, and hence can be ascribed to unwanted perturbation. Thus a perturbation can be not only detected, but its effect measured. Suitable adjustments can thus be made to the measurement from the sensing grating to compensate for the perturbation.

The arrangement of all gratings on a single substrate according to the present invention particularly facilitates the use of reference gratings, since the reference grating and the sensing grating will experience the same environment and will hence be subject to the same disturbances. To further ensure that the reference grating is perturbed in the same way as the sensing grating and to hence improve accuracy, the environment of the two gratings can be additionally harmonised by providing a sample window for the reference grating as well as for the sensing grating. A reference fluid, such as an aqueous fluid, with known properties and a known effect on the grating response can then be applied to the reference grating while a fluid sample for testing is applied to the sensing grating. However, in other embodiments, the reference grating has no window.

Preferably, the reference grating has a Bragg wavelength closely spaced from the Bragg wavelength of the sensing grating. This allows spectral discrimination between the two gratings, but also gives similar modal properties to the two gratings so that their responses and behaviour are as well-matched as possible. For example, the reference grating and the sensing grating can have Bragg wavelengths separated by 10 nm, for example a reference grating at 1540 nm and a sensing grating at 1550 nm. Separations down to about 2 nm are useful, however. The reference grating can be provided in a waveguide separate from that of the sensing grating, as in FIG. 1, or may be provided in the same waveguide as the sensing grating, as in FIG. 4. For a sensor with a plurality of gratings, a reference grating can be provided for every sensing grating. Alternatively, it may be found adequate to provide a single reference grating for a plurality of sensing gratings or for the whole sensor, perhaps in the event that it is required to detect a perturbation but not to compensate for it. In sensors having more than one reference grating, a single window can be used over all the reference gratings for application of a single reference fluid to all the reference gratings.

Figure 5A:
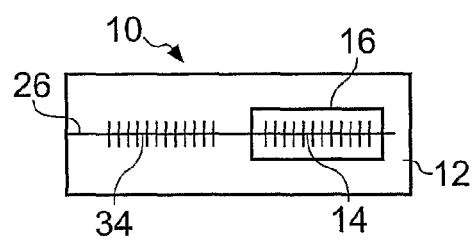
FIGS. 5A-5D show schematic representations of optical sensors according to embodiments comprising one or more reference gratings.
Figure 5B:
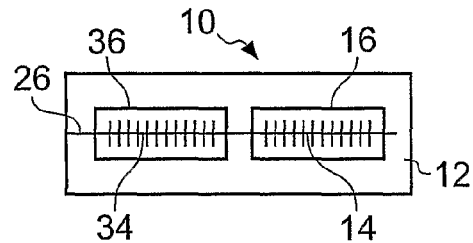
Figure 5C:
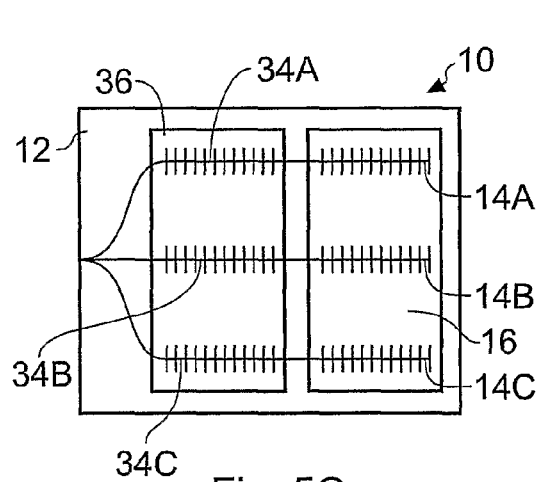
Figure 5D:
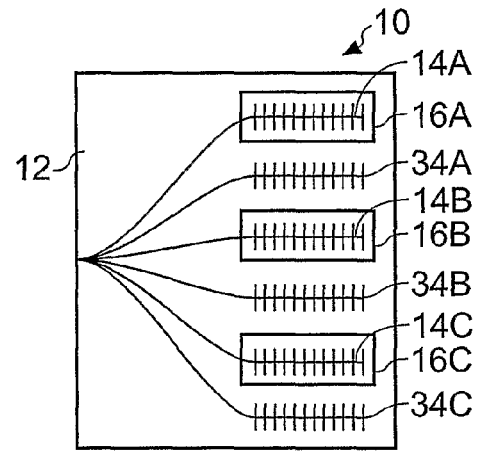

FIGS. 5A-5D show schematic representations of various examples of sensors including reference gratings. However, it will be clear from the preceding paragraph that many other permutations are possible. FIG. 5A shows a simple two grating sensor 10, in which a reference grating 34 without a window and sensing grating 14 with a sample window 16 are defined within the same waveguide 26 on a substrate 12. FIG. 5B shows a sensor 10 with the same arrangement of two gratings, but in which the reference grating 34 is provided with a window 36 to receive a reference fluid. FIG. 5C shows a larger sensor 10 having three sensing gratings 14A-14C written in three separate waveguides, but sharing a common sample window 16. Each sensing grating 14A-14C has an associated reference grating 34A-34C written in the same waveguide as the sensing grating. The three reference gratings 34 share a common window 36 for application of a reference fluid. Finally, FIG. 5D shows a sensor 10 having three sensing gratings 14A-14D each with its own sample window 16A-16D, and each written in a separate waveguide. Three reference gratings 34A-34C are also provided, but these are similarly each defined in separate waveguides, in each case adjacent to a sensing grating with which it is associated (by having the appropriate Bragg wavelength spacing, for example).

A sensor according to the invention can comprise any number of gratings, depending on the number of wavelengths of interest, the number of fluid samples to be tested at one time, and any requirement for reference gratings. As discussed, the gratings each have a different Bragg wavelength; the individual wavelengths and the total wavelength range can be selected with regard to the fluids and fluid properties to be investigated with the sensor. The wavelengths can be regularly or irregularly spaced across the range, as desired. Further, the gratings can be provided in groups according to wavelength, where gratings within a group have closely spaced wavelengths, and the groups have more widely spaced wavelengths. The wavelength of a group can be considered to be the average wavelength of all the gratings in the group. For example, a group may have a number of gratings with wavelengths spaced by wavelength separations in the range of 2-10 nm, whereas each group is spaced from the other groups by a wavelength separation of say 50 nm, 100 nm or 200 nm. Thus, the groups may have average wavelengths of 1100 nm, 1200 nm, 1300 nm, 1400 nm, 1500 nm and 1600 nm, with a first group comprising three gratings at 1098 nm, 1100 nm and 1102 nm, and a second group comprising three gratings at 1198 nm, 1200 nm and 1202 nm, etc. The close spacing within a group gives substantially similar modal properties to the waveguides, so that the same layers or the same molecular species can be detected in fluid samples, for example, with the gratings still being distinguishable by wavelength, and the wide spacing between groups can yield spectrally useful information. Also the group concept extends to sensors including reference gratings, so that each group comprises a sensing grating and a reference grating, these two having more closely spaced wavelengths than those of the various sensing gratings on the substrate.

Further with regard to external perturbations, it is possible to introduce temperature as a desirable variable into the index measurements. A temperature varying device such as a heating element or a cooling device can be thermally coupled to the optical sensor. Heat can be applied (or removed) to change the temperature of the fluid sample(s). The sensing grating(s) and any reference grating(s) also experience a change in temperature, which affects the grating periods and Bragg wavelengths, but since the gratings are on the same substrate coupled to the temperature varying device, each experiences substantially the same temperature change and shift in wavelength filtering response. Thus, the reference grating can be used to identify direct temperature-induced shifts in the sensing grating, so that temperature-induced refractive index changes in the fluid can be distinguished therefrom, and measured. Refractive index typically varies with temperature, so that the fluid sample(s) can be heated or cooled to a selection of known temperatures or through a temperature cycle while measurements of index are made, to yield the rate of change of index with temperature, dn/dT. In addition, applying the same fluid to several sensing gratings with different Bragg wavelengths adds a spectral dimension, so that measurements can be made of d(dn/dT)/dλ and d(dn/dλ)/dT. Also, different fluids can be distinguished, since even if they have identical refractive indices at one or more temperatures, they are unlikely to have the same temperature dependence of index. Further, particular heat-dependent stages in chemical and biological reactions can be identified.

Figure 6:
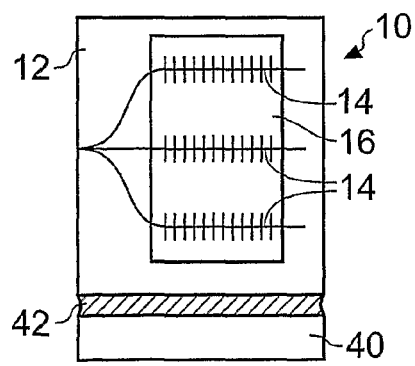
FIG. 6 shows a schematic representation of an optical sensor according to a further embodiment that includes a heating or cooling element.

FIG. 6 shows a schematic plan view representation of an optical sensor 10 that has been augmented with a heating or cooling device 40 in the above manner. The sensor comprises three sensing gratings 14 having different Bragg wavelengths and defined in different waveguides, but sharing a common sample window 16. To achieve good results using this technique, the heating or cooling device 40 should be coupled to the optical sensor 10 so as to give provide the same heating or cooling effect to all gratings (for example by use of a thermal coupling medium 42), and preferably to the whole substrate 12, to eliminate any temperature variation between the gratings that could affect the index measurements.

When designing a sensor according to the present invention, one should preferably consider a number of factors. These include operating wavelength, the refractive index and dimensions of the various waveguiding layers, and the wavelength filtering responses of the gratings. The sensitivity of the sensor to refractive index difference of fluid samples depends on how much the effective modal index of a grating is affected by the index of the fluid, which in turn depends on the amount by which the optical mode of light propagating in the grating extends out of the waveguide layers of the grating and into the fluid. Thus, control of the proximity of the fluid to the waveguide mode alters the sensitivity, and also the loss of the optical mode due to absorption in the fluid. The penetration of light into an area of lower index depends on the index difference (between the waveguide and the liquid), and the wavelength of the light. In general, longer wavelengths will penetrate further into the fluid, and hence can give higher sensitivity. However, longer wavelengths may also lead to higher loss in some cases. For example, light with a wavelength around 1.3 µm may be preferable to 1.5 µm for use with water-based fluid samples due to the considerably lower absorption at the shorter wavelength.

The design should also take into account the index or range of indices of the fluid or fluids that the sensor is intended to measure. Typically, a waveguide can be expected to have a higher index than a fluid so that the optical mode will be confined to the core and there will be little penetration into the fluid. As the refractive index of the fluid approaches that of the core the penetration depth of the mode will increase, and so will the sensitivity of the sensor to the index of the fluid. For high sensitivity, it may even be appropriate to make the grating waveguide of a material with an index lower than that of the fluid. This will lead to a lossy mode but will be very sensitive to the index of the fluid.

In a further embodiment, graded index waveguides can be used. The sample window comprises a region in which the waveguide containing the associated grating is modified to bring fluid received by the window into closer proximity with the evanescent field of light propagating in the waveguide, by removing part or all of the cladding of the waveguide and possibly part of the waveguide core as well (this is discussed further below). The window section of the waveguide thus has a different modal index from the adjacent parts of the waveguide, particularly if the cladding is removed completely to expose the core. The change in modal index is abrupt, which results in strong Fabry-Perot type fringes in the grating response, which perturb the output of the sensor. This can be addressed by varying the refractive index of the waveguide over all or part of the length of the grating, to give a graded or tapered refractive index structure. This modifies the modal index and if suitably positioned with respect to the window, can compensate for the abrupt change in modal index caused by the window, either completely or by making the change more gradual so that the fringes are less significant. For example, the taper can extend over a distance of hundreds of micrometres to a few millimetres as required, depending on the size of the window, the depth of the removed cladding and the refractive index values of the cladding and core.

Figure 7:
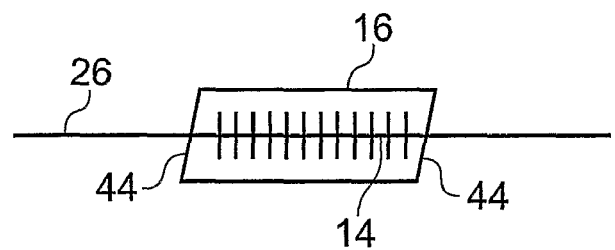
FIG. 7 shows a schematic representation of an example of a sensing window overlying a Bragg grating according to a further embodiment.

An alternative or additional approach is to reduce back-reflections by angling the sample window with respect to the underlying waveguide. Thus, at least the first edge of the window (with respect to the propagation direction in the waveguide of incoming light), and preferably the second edge (especially if more than one grating is provided along the waveguide) are positioned away from the normal to the light propagation direction. Thus, any light reflected at the interfaces where the window begins and ends is not directed back along the waveguide. An angle of a few degrees is typically adequate. FIG. 7 shows a schematic representation of a window 16 with edges 44 angled in this way with respect to a waveguide 26 containing a grating 14.

Also, optimisation of the waveguiding structure to allow single mode operation of the grating is beneficial. In general, single moded waveguides (possibly allowing for two orthogonal polarisations) will give more clearly defined reflection peaks or transmission dips in the wavelength responses of a grating. Hence, it is preferable for the waveguides of the sensor to support single mode operation, particularly where the waveguides enter the sample windows. The fluid sample in the window may have a considerably lower refractive index than the cladding material that has been removed to form the window, which can allow the waveguide to become multimoded in the window region.

Figure 8:
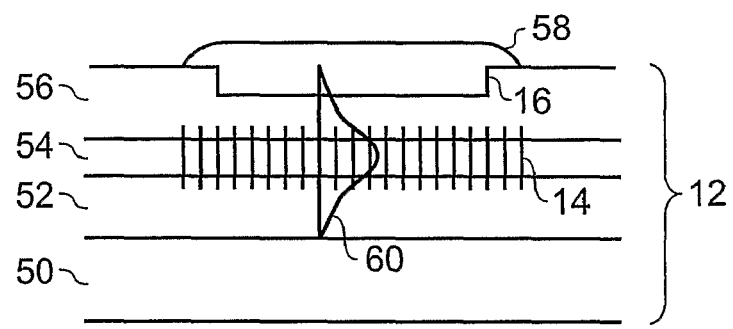
FIG. 8 shows a cross-sectional schematic representation of part of an optical sensor according to an embodiment with a first configuration of a sample window.

Any waveguide configuration that offers single mode operation may be used. One design regime for addressing this issue is illustrated in FIG. 8. This shows a schematic representation of part of a sensor, in cross-section through the length of a grating with a sample window. The sensor is formed from a substrate 12 comprising a base layer 50 supporting a lower cladding layer 52 underneath a core layer 54 underneath an upper cladding layer 56. The grating 14 is defined in the core layer 54. The sample window 16 is located over the grating 14, and is formed by partial removal of the upper cladding layer 56 overlying the grating 14 so that the cladding layer is thinner in this region than adjacent portions of the cladding layer. A sample of fluid 58 has been applied to the sample window 16. The portion of cladding in the sample window has been left relatively thick, however, so that the fluid is kept relatively remote from the core. This means that only a small portion of the evanescent field 60 of the propagating light penetrates into the fluid 58, so that the fluid has little impact on the modal profile and single mode operation is maintained.

Figure 9:
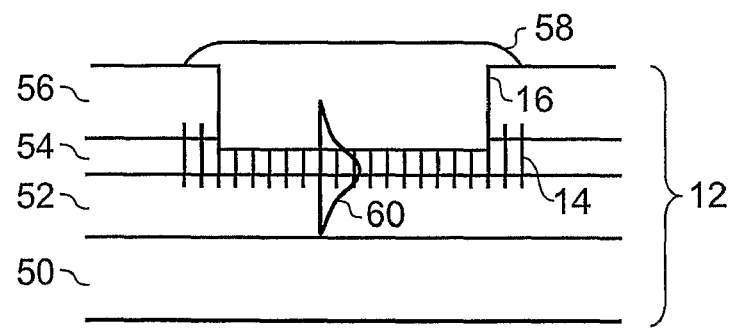
FIG. 9 shows a cross-sectional schematic representation of part of an optical sensor according to an embodiment with a second configuration of a sample window.

An alternative design regime is shown in FIG. 9. Again, this shows a schematic representation of a sensor in cross-section through the length of a grating with a window, the sensor being formed on a substrate 12 having the same structure as shown in FIG. 8. In this case, however, the sample window 16 is formed by total removal of the upper cladding layer 56 in the window region and also partial removal of the core 54, so that the core 54 has a reduced thickness in the window region compared to adjacent parts of the core. This change in core thickness maintains single mode operation, and provides a more sensitive device than that of FIG. 8. However, higher losses from absorption and scattering are likely owing to the larger proportion of the evanescent field 60 that extends into the fluid 58.

In other embodiments, a sample window may be formed by complete removal of the upper cladding layer only, leaving the core intact and of a uniform thickness.

Figure 10:
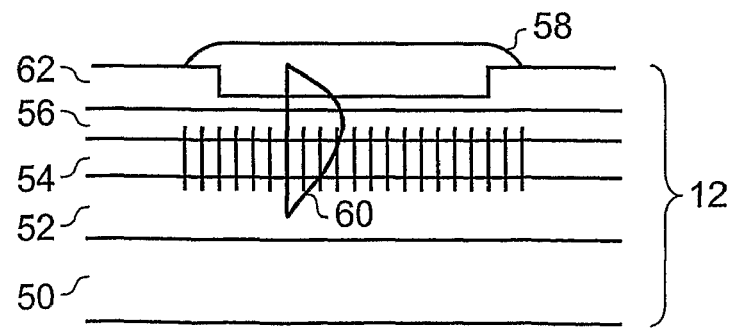
FIG. 10 shows a cross-sectional schematic representation of part of an optical sensor according to an embodiment employing a layered waveguide structure.

The amount of penetration of the optical field into the fluid can also be modified by the use of one or more additional layers in the waveguide structure to tailor the modal properties of the waveguides. For example, a high-index layer added to the cladding can be used to pull the optical field closer to the liquid to enhance sensitivity. Indium tin oxide is a suitable material for this [8], but other high index materials are not excluded. FIG. 10 shows a schematic representation of an example sensor designed in this way, again depicted as a cross-section through the length of a grating with an overlying window. The sensor is fabricated on a substrate having a layered structure as previously described with reference to FIG. 8, with a sample window 16 formed by partial removal of the upper cladding layer 56, but further including an additional upper cladding layer 62 that distorts the evanescent field 60 towards the fluid 58.

Sensors according to the present invention as described above may be used to measure the bulk refractive index of fluid samples, either as a parameter of direct interest or as an indicator of a further characteristic, such as concentration. However, in other embodiments, a surface treatment may be used to allow specificity to a particular molecule of a biological agent. To achieve this, a surface coating of a chemically selective material is applied to a sample window. The chemically selective material is such that it contains receptors that bind to a specific molecular species that may be present in a fluid sample. The binding process causes a specific change in the effective modal index that can be measured as described above. Thus, a sample containing the molecular species will give a particular output from the grating, whereas a sample lacking the molecular species will not bind to the chemically selective material and hence not modify the index in the required manner, thus giving a different output. This technique can be used for chemical and biochemical sample testing and detecting. For example, the receptors may be molecules that bind ligands present in the sample, or the receptors may be antibodies that bind antigens in the sample, or vice versa [9]. According to various embodiments of the invention, one, some or all of the sample windows associated with sensing gratings on a sensor can be provided with a layer of chemically selective material. Also, various sample windows can have different chemically selective materials.

In a further embodiment, a metallic film can be applied to a sample window as a surface layer or coating. This gives a grating that operates as a surface plasmon sensor, in which the metallic layer supports a surface plasmon that is modified by the presence of a fluid in the sample window. This modification produces a corresponding change in the effective modal index, which can be measured as described above owing to the resulting change in the Bragg wavelength of the sensing grating. Any metal that supports surface plasmons can be used, such as gold, silver, aluminium and platinum. Gold is particularly suitable for testing biological fluid samples since it is biologically compatible. Also, gold is expected to increase the sensitivity of the grating. According to various embodiments of the invention, one, some or all of the sample windows associated with sensing gratings on a sensor can be provided with a metallic layer, and different sample windows can have different metals.

Figure 11:
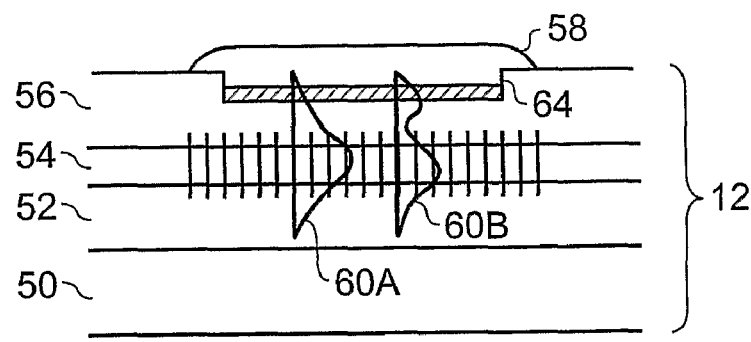
FIG. 11 shows a cross-sectional schematic representation of part of an optical sensor according to an embodiment with a third configuration of a sample window.

FIG. 11 shows a schematic representation of part of an example sensor having a structure for chemically selective sensing or surface plasmon sensing, again depicted as a cross-section through the length of a sensing grating. The sensor is fabricated on a substrate having a layered structure as previously described with reference to FIG. 8. In this case, however, a surface coating or layer 64 is applied over the sample window, so that a fluid sample 58 sits on top of the coating. The coating 64 is a chemically selective material capable of binding with molecules in the fluid sample 58 in the case of a chemically selective sensor, or a metallic film in the case of a surface plasmon sensor. In the former case, the evanescent wave 60A is substantially undistorted compared to there being no coating. In the latter case the wave 60B has subsidiary peak in the metallic film owing to the surface plasmon; this increases the sensitivity owing to a greater proportion of the optical field being in close proximity to the fluid.

There are many possible configurations for a multiwavelength sensor according to the present invention. Any or all of the above embodiments can be integrated in a single sensor. A range of combinations of different grating wavelengths and sample windows can be provided, for example configurations with different sensitivities, or windows with different chemically selective coatings (for testing a single biological sample for different compounds, for example) or windows with different surface plasmon metallic films, or any combination of these. Also, information can be gained by analysing the changes to the grating responses from molecules in the samples, since the ability to record information at multiple wavelengths can be used to gain insight into molecular species present in a fluid. For example, the addition of water to another liquid may cause greater changes at 1400 nm and 1500 nm from the OH bonds than at 1100 nm and 1200 nm. Similarly, the presence of C—H bonds and C=C double bonds could be detected at different wavelengths to yield information about multiphase and multi-component liquids. These changes typically result from both additional absorption and modified refractive index in spectral regions where strong molecular resonances occur. Such information has application in sensing contamination in industrial systems.

Sensitivity can be varied from grating to grating by varying the thickness of the cladding layer in the sample windows to give different penetration depths of the optical field into the fluid sample. As well as giving different sensitivities, the different penetration depths allow different depths in a fluid sample to be interrogated to investigate layers within a sample. For example, it may be that the fluid adheres to the surface of the window (perhaps if a chemically selective coating is included) and gives a different index to the bulk of the fluid sample. The gratings could have widely spaced wavelengths, or alternatively, a selection of different gratings of very closely spaced wavelength (2 nm separation, for example), each with a different cladding thickness, could be used to obtain information about the build-up of molecular species. The closely spaced wavelengths have substantially the same modal confinement and hence field penetration depth and can "see" the same molecular species, but can be distinguished in detection to allow each grating to be analysed separately. Further groups of gratings with wavelengths closely spaced around a wavelength more widely spaced from the first group can be provided to give a spectral dimension to the measurements.

Figure 12:
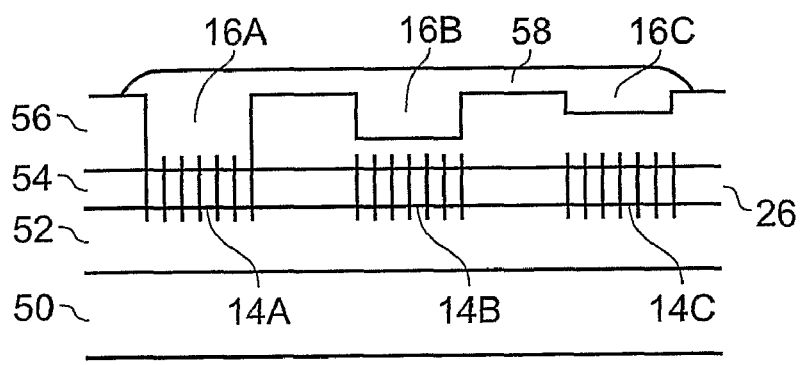
FIG. 12 shows a cross-sectional schematic representation of part of an optical sensor according to an embodiment incorporating sample windows of varying sensitivity.

FIG. 12 shows a schematic cross-section through part of a sensor having gratings with windows of different cladding thickness. The sensor is formed on a layered substrate having the same structure as that described with reference to FIG. 8. In this example, three gratings 14A-14C are provided, written sequentially along the length of the core 54 of a single waveguide 26. Each grating has a different Bragg wavelength, chosen to give appropriately independent responses, in particular so that propagation through earlier gratings does not materially affect the grating responses. Each grating 14 has a sample window 16; the left hand window 16A is formed by total removal of the upper cladding layer 56, and the windows 16B and 16C are formed by partial removal of the upper cladding layer 56, with a thinner portion of cladding used for the middle window 16B than for the right hand window 16C. This means that the evanescent wave of light propagating in the waveguide and the gratings penetrates further into the fluid 58 received in the window for the right hand grating 14A than for the middle grating 14B, which in turn has a greater penetration depth that for the right hand grating 14C. The greater field penetration depth results in a greater sensitivity to the fluid index, and if the layer of fluid at the bottom of the windows is different from that of the bulk of the fluid (as for example if a biological layer preferentially adheres to the window surfaces), additional information about the fluid structure can be obtained.

In all embodiments, a wide range of fluids can be measured, detected, or monitored. Suitable media include liquids, two-phase liquids, colloids, liquid-solid phase transitions, super-critical gases, emulsions and biological samples. For example, a potential application of the multiple wavelength measurements that can be obtained is in an ice formation sensor in which the phase transition from water to ice can be monitored to reveal ice build-up on aircraft.

In addition, or instead of, measuring the central Bragg wavelengths of the gratings, one can measure the grating bandwidths (possibly at different widths, such as 3 dB and 10 dB) and the lineshape of the grating responses to gain additional information about fluid samples. For example, a strongly absorbing fluid will limit the effective grating length causing a broader spectral peak in the grating response. Variation of the fluid along the length of the grating (as would occur if large molecules attached to the window surface, or if a two-phase liquid was present) will cause a varying waveguide index along the grating, observed as an alteration in the grating lineshape. A more complex analysis may include fitting a model to the measured spectral output reflected by a grating that includes loss and random variation of index along the grating, and possibly at other locations within the sensor through which the detected light has propagated.

Optical sensors according to the present invention may be used in any situation in which it is necessary to determine the refractive index of one or more fluids or fluid samples, or to determine properties or features of a fluid that vary with refractive index, or to identify a fluid or distinguish between fluids. Applications in fields including physics, chemistry, biology, medicine, pharmaceuticals and food science are all possible. As an example application, a sensor may be used in the control of an industrial or manufacturing process. A fluid or fluids used in or made by the process can be repeatedly tested using one or more sensors, and the results used to control subsequent stages of the process, perhaps by sending software commands to the process apparatus. For example, the end point of a process can be determined, or unwanted events such as contamination can be detected. The measurements may comprise part of a feedback loop, for example, to provide constant monitoring of a fluid composition in a manufacturing process. Use of sensors in this way can be used to automate a process, or to improve accuracy.

In the event that more than one sensor is used, the sensors can be combined into a network to provide a control system for the process. A number of sensors may be remotely deployed throughout the process apparatus, and connected to a central control hub. The hub contains one or more optical sources to generate light containing wavelengths covering the bandwidths of each sensor grating in the control system, and a detector such as an OSA to receive and spectrally analyse light reflected from the gratings. Also, an optical routing device is included to take light from the optical source(s) and direct it to the sensors, and to receive light reflected from the sensors and direct it to the OSA. Optical fibres can be used to connect the various components to the central control hub. The OSA, perhaps in combination with a central processing unit or an equivalent processing device, analyses the reflected light, determines the fluid property being monitored, and outputs one or more control signals to the process apparatus based on the value of the fluid property that has been determined.

The optical routing device can be configured in any manner appropriate to handle the various wavelengths of light and the number of sensors. A first example is a fibre optic switch configured to individually address each of the sensors (sequentially or otherwise as required) by making an optical connection between the optical source and a particular sensor. In this case, each of the sensors can be identical with regard to their grating Bragg wavelengths since the switch provides unique addressing. A second example is a series of optical splitters that divide the light from the light source according to wavelength and direct it to the appropriate sensors, where the sensors each have gratings with different Bragg wavelengths. The splitters operate in reverse to recombine the reflected light. Loss of optical power will result from the splitting and recombining, however. If this is unacceptable, an alternative approach for sensors with different Bragg wavelengths is to use a wavelength demultiplexing component such as an arrayed waveguide grating to uniquely match wavelengths to sensors.

Figure 13:
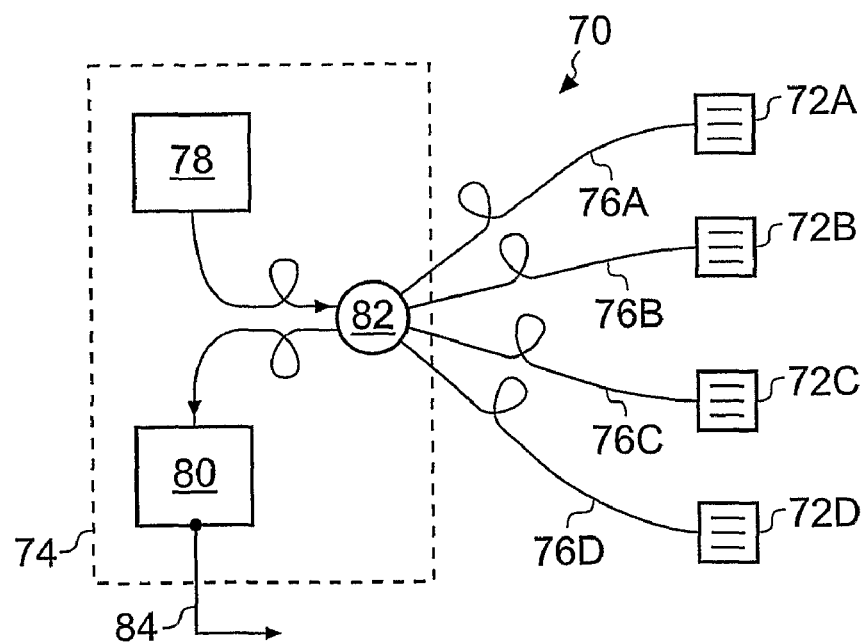
FIG. 13 shows a schematic representation of a process control system incorporating optical sensors according to embodiments of the invention.

FIG. 13 shows a simplified schematic representation of a process control system according to an embodiment of the present invention. The control system 70 comprises four sensors 72A-72D according to any of the previously described examples and embodiments, deployed as appropriate throughout apparatus operable to carry out the process. Each sensor is connected to a single central control hub 74 by an optical fibre 76A-76D. The hub comprises an optical source 78, a spectrally resolving optical detector 80, and a optical routing device 82. The central control hub 74 is represented by a dotted line, and may or may not comprise an enclosure or housing to group the various components. The optical routing device 82 receives light from the optical source 78, directs it to the sensors 72 via the optical fibres 76 (either by switching to connect a particular sensor or by dividing the light according to wavelength, according to the examples in the preceding paragraph), receives light returned from the sensors 72 via the optical fibres 76, and directs it to the detector 80. The detector analyses the returned light to determine a property of fluid samples tested by one or more of the sensors and generates a corresponding control signal, which is supplied to the apparatus via a control line 84.

Although a process control system can be implemented using a single sensor, the concept of connecting a number of sensors via an optical routing device is widely applicable. Thus the present invention further extends to optical sensor networks, in which a plurality of sensors (which may be identical or different) are connected to an optical routing device which receives light from an optical source and distributes it to the relevant sensors and collects light reflected from the sensor gratings and delivers it for spectral analysis. The results of the analysis may be provided to a processor such as a computer processor which is programmed to determine properties of fluids tested by the sensors from the Bragg wavelengths shifts apparent from the spectral analysis.

A network of this type may be used to integrate a large number of gratings with different wavelengths and different window types in the event that it is not practical to accommodate all the gratings on one sensor substrate, and/or to provide centralised operation of a number of sensors that need to be deployed in diverse locations.

Any fabrication techniques suitable for making gratings and waveguides and connecting them in the required manner can be employed to fabricate optical sensors according to the invention described thus far. For example, lithography and etching may be used. A particularly suitable technique is that of direct ultraviolet (UV) writing, using UV laser radiation to increase the refractive index of silica to write both channel waveguides and gratings into a single substrate [10].

The direct UV writing fabrication technique is particularly advantageous because it allows long high quality planar gratings to be written. This gives gratings with a very narrow linewidth, leading to sensors with high sensitivity. The bandwidth $\Delta\lambda$ of a Bragg grating of Bragg wavelength $\lambda_{Bragg}$ is given by [11]:

$$\Delta\lambda = \lambda^2_{Bragg}/2n_{eff}L(\pi^2+(\kappa L)^2)^{1/2}$$

where $\kappa$ is the coupling coefficient defined by $$\kappa = \pi n \delta n \eta / \lambda_{Bragg} n_{eff}$$

and n is the refractive index of the waveguide cladding, $n_{eff}$ is the effective modal index, $\delta n$ is the magnitude of the index modulation in the grating, $\eta$ is the overlap integral between forward and backward propagating modes, and L is the length of the grating. Thus, the bandwidth depends on the length of the grating for weak gratings and on the index modulation for stronger gratings. The resolution of the optical sensor to fluid refractive index change is related to the minimum resolvable wavelength shift, and thus it is desirable to use long gratings with narrow spectral bandwidths (wavelength filtering response).

For example, sensors may be fabricated using the direct UV writing technique to write channel waveguides and gratings into a silica on silicon three layer wafer. This has an underlying silicon wafer base that provides a robust carrier for subsequent deposition of doped silicon oxide (doped silica) to form the various waveguiding layers. Silicon is compatible with processing for the growth and annealing of oxide layers. In addition it is possible to incorporate other elements into the silicon wafer, such as MEMS structures for flow control, metering and heating of fluid samples, and for additional integrated measurements such as in-situ thermal measurements. Also, a silicon wafer has a lower thermal expansion coefficient than silica, so that after annealing the silica layers are under compressive stress at room temperature, which helps to make the layers robust. It is, however, possible to grow the silica layers on materials other than silicon, including but not limited to silica.

The layers can be grown by a number of techniques. The starting point is the silicon base which is conventionally thermally oxidised in a steam environment to grow a thin oxide layer on its surface. This first layer helps the growth and consolidation of the later, thicker oxide layers. These layers may be deposited using techniques such as flame hydrolysis deposition (FHD), low pressure chemical vapour deposition (LPCVD), plasma enhanced chemical vapour deposition (PECVD), direct bonding or ion exchange. For direct UV writing, a photosensitive layer is required. This may be achieved with a three-layer structure in which the upper and lower layers are cladding layers and the central layer is a core layer that is doped with a material to promote sensitivity such as germanium oxide. Any of the layers may also include additional dopants to control refractive index, fabrication temperature, etc. Commonly, phosphorus, boron, tin and titanium are doped into silica. Also, doping the layers with deuterium at high pressure for several days can be used to increase the photosensitive response. Hydrogen is an alternative photosensitiser. Alternatively, rapid thermal processing can be employed to increase photosensitivity.

Next, channel waveguides are written into the layered substrate. For direct UV writing, a substrate is translated under a focussed spot of UV laser radiation, the spot having dimensions approximately related to the desired channel dimensions. Preferably, the channels are designed to be single mode to give a strong Bragg grating response. The gratings are defined using a spot with an intrinsic interference pattern. The laser intensity is modulated at precisely controlled positions, allowing a grating to be written simultaneously with the waveguide containing it. Computer control of the writing apparatus allows precise control of the grating period and length (and hence Bragg wavelength and bandwidth) and optical waveguide shape. Thus, single-substrate optical sensors comprising two or more gratings connected by channel waveguides such as those described above can be written with a single fabrication process.

After waveguide and grating formation, the substrate is processed to form the sample window or windows. Etching with hydrofluoric acid can be used to remove the cladding material. The window region is defined by masking the non-window parts of the substrate with photoresist, before etching. The photoresist may be defined using lithographic processes that are related to the positioning of the waveguides to place the windows in correct registration with the grating positions. If several windows with different cladding depths are required, the window regions can be etched to different depths using techniques such as depositing differently etch-resistant layers before etching, suspending etching at appropriate times and covering sufficiently etched windows with etch-resistant material, lowering the substrate into an etching liquid in steps, or pulling a masking plate across the substrate in steps in the case of gas phase etching.

REFERENCES

[1] J Bowen, L J Noe, B P Sullivan, K Morris, V Martin and G Donnelly, "Gas phase detection of trinitrotoluene utilizing a solid-phase antibody immobilized on a gold film by means of surface plasmon resonance spectroscopy", Appl. Spectrosc., 57(8), 906-914, 2003

[2] R G Heideman, R P H Kooyman and J Greve, "Performance of a highly sensitive optical wave-guide Mach-Zehnder interferometer immunosensor", Sensors and Actuators B-Chemical, 10(3), 209-217, 1993.

[3] K Tiefenthaler and W Kukosz, "Integrated optical switches and gas sensors", Optics Letters, 10(4), 137-139, 1984.

[4] W Lukosz, D Clerc and PhM Nellen, "Input and output grating couplers as integrated optical chemo- and biosensors", Sensors and Acuators A, 25-27, 181-184, 1991.

[5] A Asseh, S Sandgren, H Ahlfeldt, B Sahlgren, R Stubbe and G Edwall, "Fiber optical Bragg grating refractometer", Fiber and Integrated Optics, 17(1), 51-62, 1998.

[6] A Iadicicco, A Cusano, A Cutolo, R Bemini and M Giordano, "Thinned fiber Bragg gratings as high sensitivity refractive index sensor", IEEE Photonics Technology Letters, 16(4), 1149-1151, 2004.

[7] X Chen, K Zhou, L Zhang and I Bennion, "Optical chemsensors utilizing long-period fiber gratings UV-inscribed in D-fiber with enhanced sensitivity through cladding etching", IEEE Photonics Technology Letters, 16(5), 1352-1354, 2004.

[8] B J Luff, J S Wilkinson, G Perrone, "Indium tin oxide overlayered waveguides for sensor applications", Applied Optics, 36(27), 7066-7072, 1997.

[9] W Lukosz, "Integrated optical chemical and biochemical sensors", Sensors and Actuators B, 29, 37-50, 1995.

[10] GB 2 395 797

[11] R Kashyap, "Photosensitive optical fibers: Devices and applications", Optical Fiber Technology, 1, 17-34, 1994

The invention claimed is:

1. An optical sensor comprising:
   a substrate;
   at least two planar Bragg gratings defined within one or more optical waveguides in the substrate, each Bragg grating having a wavelength filtering response that varies with an effective modal index experienced by light propagating in the Bragg grating and that has a characteristic Bragg wavelength different from the Bragg wavelengths of the other Bragg gratings; and
   at least one sample window overlying and associated with at least two of the Bragg gratings and arranged to receive a sample of fluid such that the presence of a sample of fluid affects the effective modal index experienced by light propagating in the associated Bragg gratings and hence modifies the wavelength filtering response of those Bragg gratings;
   the Bragg gratings being arranged to receive light from a light source, filter the light by reflection, and output the filtered light reflected from the Bragg gratings for detection by a spectrally resolving optical detector or an optical power detector.

2. An optical sensor according to claim 1, in which sample windows are associated with each of the at least two Bragg gratings, so that all of the least two Bragg gratings may be provided with a sample of fluid.

3. An optical sensor according to claim 1, in which the at least one sample window comprises a single sample window shared by all of the at least two Bragg gratings so that a sample of fluid received by the sample window affects the effective modal index of light propagating in all of the at least two Bragg gratings.

4. An optical sensor according to claim 1, in which the at least two Bragg gratings comprise one or more pairs of Bragg gratings, each pair of Bragg gratings comprising a sensing grating having an associated sample window and a reference grating, the sensing grating and the reference grating having Bragg wavelengths sufficiently closely separated that the gratings have substantially the same modal confinement.

5. An optical sensor according to claim 4, in which the sensing grating and the reference grating have Bragg wavelengths separated by an amount in the range of 2 to 10 nm.

6. An optical sensor according to claim 4, in which the reference grating has an associated sample window, separate from the sample window associated with the sensing grating.

7. An optical sensor according to claim 4, in which the reference grating and the sensing grating are defined within a single waveguide.

8. An optical sensor according to claim 1, in which the at least two Bragg gratings comprise a plurality of Bragg gratings divided into groups of Bragg gratings, the Bragg gratings within each group having Bragg wavelengths separated by a first separation, and each group having an average Bragg wavelength separated from average Bragg wavelengths of other groups by a second separation greater than the first separation.

9. An optical sensor according to claim 8, in which the second separation is at least ten times greater than the first separation.

10. An optical sensor according to claim 8, in which the first separation is in the range of 2 to 10 nm.

11. An optical sensor according to claim 1, in which the one or more optical waveguides are configured for single mode propagation of light.

12. An optical sensor according to claim 1, in which at least one of the at least one sample windows comprises a portion of a cladding layer overlying a core of the optical waveguide in which the associated Bragg grating(s) are defined, such that a sample of fluid received by the sample window is in contact with the cladding layer.

13. An optical sensor according to claim 12, comprising two or more sample windows in each of which the portion of the cladding layer has a different thickness.

14. An optical sensor according to claim 1, in which at least one of the at least one sample windows comprises an exposed portion of a core of the optical waveguide in which the associated Bragg grating(s) are defined, such that a sample of fluid received by the sample window is in contact with the core.

15. An optical sensor according to claim 14, in which the exposed portion of the core has a thickness less than a thickness of the core in adjacent portions of the optical waveguide in which the associated Bragg grating(s) are defined.

16. An optical sensor according to claim 1, in which the or each Bragg grating having an associated sample window is defined in an optical waveguide having a core that has a tapering variation in refractive index along its length, to reduce abrupt changes in the effective model index at edges of the sample window.

17. An optical sensor according to claim 1, in which the at least one sample window has one or more edges that are angled with respect to a light propagation direction in the optical waveguide in which the associated Bragg grating is defined, to reduce reflections of light propagating in the Bragg grating.

18. An optical sensor according to claim 1, in which the one or more optical waveguides comprise one or more layers that modify waveguiding properties of the one or more optical waveguides.

19. An optical sensor according to claim 1, in which at least one of the at least one sample windows is provided with a surface coating of a chemically selective material operable to bind with molecules that may be present in a sample of fluid to be received by the sample window, the binding causing an alteration of the effective modal index of light propagating in the associated Bragg grating(s).

20. An optical sensor according to claim 1, in which at least one of the at least one sample windows is provided with a surface layer of a metal having a surface plasmon that may be altered by a sample of fluid to be received by the sample window, the alteration in the surface plasmon causing an alteration of the effective modal index of light propagating in the associated Bragg grating(s).

21. An optical sensor according to claim 1, and further comprising a heating or cooling device operable to modify the temperature of the substrate such that each of the at least two Bragg gratings have substantially the same temperature.

22. An optical sensor according to claim 1 and further comprising one or more light sources operable to deliver light to the at least two Bragg gratings such that each Bragg grating receives light having a spectral bandwidth covering at least part of its wavelength filtering response.

23. An optical sensor according to claim 1, and further comprising a spectrally resolving optical detector operable to detect and spectrally resolve light output by each of the Bragg gratings.

24. A process control system operable to control apparatus for performing a process, comprising:
- at least one optical sensor according to claim 1 and arranged to receive samples of fluid utilised in or generated by the process;
- an optical source operable to generate light covering the wavelength filtering response or responses of the Bragg gratings of the at least one optical sensor;
- a spectrally resolving optical detector operable to receive and perform spectral analysis of light from the at least one optical sensor and to generate one or more control signals for controlling the apparatus in response to the analysis; and
- an optical routing device connected to the at least one optical sensor, the optical source and the optical detector, and operable to receive light from the optical source, distribute the light to the at least one optical sensor, receive light output by the at least one optical sensor, and deliver the output light to the optical detector.

25. An optical sensor network comprising:
- a plurality of optical sensors according to claim 1;
- an optical routing device connected to each of the plurality of optical sensors and operable to receive light from a light source, distribute the light to the plurality of optical sensors, receive light output by the plurality of optical sensors, and output the received light for spectral analysis.

26. An optical sensor network according to claim 25, and further comprising:
- an optical source operable to generate light covering the wavelength altering responses of the Bragg gratings of the plurality of optical sensors and arranged to deliver the light to the optical routing device;
- a spectrally resolving optical detector arranged to receive light output from the optical routing device, and operable to perform spectral analysis of the light.

27. An optical sensor network according to claim 26, and further comprising a processor arranged to receive results of spectral analysis from the optical detector and operable to determine one or more properties of a sample or samples of fluid applied to the plurality of optical sensors from the results.

* * * * *